United States Patent [19]

Knifton

[11] 4,132,744
[45] Jan. 2, 1979

[54] PROCESS FOR SEPARATING LIQUID OLEFIN-PARAFFIN MIXTURES

[75] Inventor: John F. Knifton, Austin, Tex.

[73] Assignee: Texaco Inc., New York, N.Y.

[21] Appl. No.: 859,498

[22] Filed: Dec. 12, 1977

[51] Int. Cl.² .............................................. C07C 7/16
[52] U.S. Cl. .............................................. 260/677 A
[58] Field of Search ..................... 260/677 A, 681.5 C

[56] References Cited

U.S. PATENT DOCUMENTS

| | | | |
|---|---|---|---|
| 3,527,831 | 9/1970 | Blytas | 260/677 A |
| 3,755,487 | 8/1973 | Jahnig et al. | 260/677 A |
| 4,025,574 | 5/1977 | Tabler et al. | 260/677 A |

Primary Examiner—C. Davis
Attorney, Agent, or Firm—Thomas H. Whaley; Carl G. Ries; Bernard Marlowe

[57] ABSTRACT

This invention relates to a process for selectively separating olefins from liquid, aliphatic olefin-paraffin mixtures, said olefins and paraffins each containing from 6 to 20 carbon atoms. Separation is effected by a liquid-liquid extraction technique, using solutions of silver or copper salts in alkanols, or mixed alkanol-aliphatic polyethers solvents, as the extracting media.

10 Claims, No Drawings

PROCESS FOR SEPARATING LIQUID OLEFIN-PARAFFIN MIXTURES

SUMMARY OF INVENTION

This invention concerns a process for the separation of liquid olefins from paraffinic contaminents having the same or similar carbon content.

More particularly, this invention relates to the separation of aliphatic olefins, having a carbon content of from $C_6$ to $C_{20}$, from liquid paraffinic hydrocarbon materials, also containing 6 to 20-carbon atoms per molecule, by a liquid-liquid extraction technique employing solubilized silver and copper complexes in alkanol or alkanol-aliphatic polyether solvents as the extracting media.

BACKGROUND OF INVENTION

Olefins, particularly linear alpha (terminal) and internal aliphatic olefins are useful petrochemical building blocks of significant industrial importance because of their good chemical reactivity, relatively low cost and availability. Important industrial applications for liquid olefinic hydrocarbons of six or more carbons per molecule include (a) conversion of the $C_7$–$C_9$ range, by Oxo technology, to primary alcohols for plasticizer production, (b) the conversion of $C_{11}$–$C_{14}$ range to linear alkylbenzenes for use in biodegradable detergent applications, (c) hydroformylation of $C_{11}$–$C_{18}$ olefins to primary alcohols for use as their ethoxylated, sulphated and sulphonated derivatives in the detergent field, together with (d) miscellaneous applications as chemical intermediates in textile finishes, synthetic waxes and petroleum additives.

Unfortunately, the olefins prepared by dehydrogenation of paraffinic materials, particularly linear n-paraffins, are normally generated in low concentrations and are available only in the presence of much larger quantities of the corresponding saturated paraffinic starting material. Furthermore, where the carbon content of the paraffinic contaminent in the stream or charge stock is close to the carbon range of the olefins, separation of the two fractions cannot readily be achieved by distillation means.

Recently, the applicants have developed a liquid-liquid extraction procedure for separating liquid, aliphatic olefins of carbon number greater than six, from liquid olefin-paraffin mixtures that cannot readily be separated by distillation. The separation technique utilizes silver and copper salts solubilized in a low molecular weight alkanol or alkanol-polyether solvent mixtures.

DESCRIPTION OF THE PREFERRED EMBODIMENTS

In the extraction procedure of this invention, the separation of aliphatic olefin-paraffin mixtures, each containing from 6 to 20 carbon atoms is effected using an extractant media comprising one or more Group IB metal salts solubilized in an alkanol, or alkanol-rich polyether solvent system, by the procedure of:

(a) Contacting said olefin-paraffin mixture with the solution of Group IB metal salt in the alkanol-containing solvent media, to form a two-phase mixture.

(b) Rapidly agitating said mixture to achieve an equilibrium distribution of the olefin and paraffin fractions between the two phases.

(c) Separating the two phases, and recovering the olefin-rich concentrate from the Group IB metal-containing extractant phase.

In the favored practice of this invention, olefins are separated from liquid olefin-paraffin mixtures wherein said olefins and paraffins contain from 6 to 20 carbon atoms per molecule, and the total olefin content is from 1 to 50%, by the process of:

(a) Contacting said mixtures of olefins and paraffins with an extractant, non-aqueous solution of Group IB metal salts, said metal salts being selected from the group consisting of silver and copper salts, and said non-aqueous solvent systems being selected from alkanols, containing 1 to 4 carbon atoms, or optionally, from alkanol-polyether solvent-mixtures, to form a two-phase mixture.

(b) Agitating said two-phase mixtures, at temperatures ranging from 0° to 70° C., to form an extractant phase, containing the copper or silver salt, which is olefin rich and paraffin poor, and a paraffinic phase which is paraffin-rich and olefin-poor.

(c) Separating the extractant, olefin-rich, phase from the paraffinic rich phase and isolating the olefin concentrate contained in the extractant phase by fractional distillation.

In order to aid in the understanding of the inventive concept, the following supplemental disclosure is submitted:

(A) Olefin-Paraffin Mixtures — It is believed that a broad range of $C_6$–$C_{20}$ aliphatic olefin structures may be separated from paraffinic contaminents by the extraction technique described herein. Suitable classes of olefin include linear α-olefins, internal olefins, branched-chain olefins and cyclic olefins having a b.p. >30° C. at 1 atm pressure. These may be present either as discrete, single-carbon olefin isomers, as in the case of 1-decene, 2-decene, 1-tetradecene, 5-dodecene, 2-octene and 2-hexadecene, or they may be in the form of olefin mixtures, such as, for example, mixed internal and terminal decenes, mixed tetradecenes or $C_{10-20}$ internal olefins such as are produced by paraffin dehydrogenation. Likewise, the paraffinic contaminant may be present as a single compound, or in the form of mixtures having 6 to 20 carbon atoms per molecule.

A preferred class of olefin-paraffin mixture for this extraction technique is the terminal (alpha) and internal olefins containing 10 to 20 carbon atoms per molecule and prepared by vapor-phase dehydrogenation of paraffinic materials as set forth, for example in U.S. Pat. No. 3,458,592. A typical example is the olefin-paraffin mixture prepared by dehydrogenation of $C_{10-14}$ n-paraffins.

(B) Extractant System — The extractant systems are non-aqueous, alkanol-rich solutions of silver or copper salts. Said copper and silver salts are solubilized in one or more of the lower alkanols that, optionally, may also contain up to 50% (v/v) of a liquid, saturated, aliphatic polyether cosolvent. Suitable alkanol solvents used to dissolve the silver or copper salts and effect the desired olefin-paraffin separations include the lower alkanols containing 1 to 4 carbon atoms. Examples include methanol, ethanol, n-propanol, n-butanol, tert-butanol and iso-propanol. Suitable polyether cosolvents include 1,2-dimethoxyethane, diethyleneglycol dimethyl ether (diglyme), triethyleneglycol dimethylether (triglyme), p-dioxane, 1,2-diethoxyethane, diethyleneglycol monomethylether, diethyleneglycol monobutylether, together with polyethylene glycols such as tetraethyleneglycol.

(C) Group IB Metal Salts — Metal salts employed in this extraction process to aid in the separation of liquid olefin-paraffin mixtures include salts and complexes of silver and copper. Suitable examples include silver nitrate, silver perchlorate, silver acetylacetonate, silver difluoride, silver lactate, silver propionate, silver chlorate, silver acetate, silver tetrafluoroborate, copper acetylacetonate, copper difluoride, copper 2-ethylhexanoate, copper chloride, cuprous acetate, cupric acetate, copper sulphate, copper trifluoroacetate, cuprous ammonium acetate, cuprous hexafluorophosphate, cuprous tetrafluoroborate and copper nitrate.

(D) Experimental Conditions — Temperatures employed in the extraction process are not critical. Usually temperatures ranging from 0° C. up to 70° C. may be employed, but temperatures above ambient appear to offer no distinct advantages. Likewise, normally atmospheric or near atmospheric pressures are employed. Extraction times are then quite brief and dependent primarily upon the nature of the metal salt used and the choice of solvent.

After extraction, the olefin-rich fraction may be isolated from the extractant phase either by fractional distillation, or by displacement via a second extraction step using one or more suitable light solvents.

(E) Ratio of Silver or Copper Salt to Olefin present — Ordinarily equimolar ratios of the silver or copper salts in the extracting phase to olefin present in the original paraffin phase are used. Higher or lower ratios can be used if desired. However, higher ratios of the silver or copper salts to olefin appear to be wasteful and lower ratios most often lead to lower partition coefficients (see Examples 5, 6 and 18) hence higher nor lower ratios of salt are not generally used.

GENERAL PROCEDURE FOR THE PRACTICE OF INVENTIVE PROCESS

To a conveniently sized reaction vessel equipped with efficient means of stirring, heating, cooling and provided with a means of introducing a gas, or mixture of gases, to the system, is charged with a mixture containing the desired aliphatic olefins and paraffin contaminants. Preferably, the olefin-paraffin mixture is saturated with inert gas (such as nitrogen, argon, neon and the like) prior to introduction of the extracting, alkanol-rich solution containing the silver or copper salts used in the extraction step(s). The extractant mixture, when added to the paraffin-olefin, forms a 2-phase system which is stirred rapidly at about room temperature for a period of time usually ranging from ¼ hour to 1 hour to effect extraction. However, additional stirring times do not appear to be harmful. The lighter or top, paraffinic, phase of the two-phase system containing primarily the paraffinic contaminants is separated from the olefin-rich extractant phase. The extract phase is then distilled under reduced pressure (preferably between 1–20 cm Hg or lower) to remove the alkanol and/or polyether, and the silver or copper salts are recovered by filtration. The filtrate consists of the concentrated olefin fraction.

EXAMPLE 1

Extraction of 1-Decene from a 1-Decene, n-Dodecane Mixture

An appropriately sized reaction vessel equipped with means for introducing gas, as well as means of agitating, heating and cooling, is charged with a nitrogen-saturated solution of silver nitrate (8.5 g 50 mmole) in methanol (150 ml) and 1,2-dimethoxyethane (50 ml). A mixture of 1-decene (18.9 ml, 100 mmole) and n-dodecene (40 ml) is added under nitrogen, and the two phase mixture stirred rapidly for 30 minutes at 22° C. The paraffinic phase (30 ml) is then separated from the extracting phase, and the extract phase distilled under reduced pressure (1–20 cm) to recover the methanol and 1,2-dimethoxyethane. The silver salt is recovered from the residue by filtration, the filtrate (28 ml) consists of the 1-decene concentrate fraction.

Analysis by chromatography (glc) and titration (Br number) shows the paraffinic phase after extraction to contain 18% 1-decene in n-dodecane. The concentration of 1-decene in the extract phase is 42%.

EXAMPLE 2

Procedure for Extracting $C_{10}$–$C_{14}$ Olefins from a $C_{10}$–$C_{14}$ n-Paraffin Mixture Using the general procedure described in Example 1, a nitrogen-saturated solution of silver nitrate (8.50 g, 50 mmole) in methanol (150 ml) and 1,2-dimethoxyethane (50 ml) is added, under nitrogen gas to 100 ml of dehydrogenated $C_{10}$–$C_{14}$ n-paraffin mixture containing approximately 50 mmole of $C_{10}$–$C_{14}$ olefin. The two-phase system is continuously stirred at 20° C.–22° C. for about 1 hour. The lighter paraffinic phase (83 ml) is separated from the heavier extractant layer containing the olefin mixtures, methanol and 1,2-dimethoxyethane. The extract phase is distilled under reduced pressure (1–20 cm Hg) to strip out the methanol and 1,2-dimethoxyethane fractions. The silver salt is recovered from the residual material by filtration, leaving a filtrate (5 ml) consisting of the concentrated olefin fraction.

EXAMPLE 3

Multiple Extraction of $C_{10}$–$C_{14}$ Olefins from a $C_{10}$–$C_{14}$ n-Paraffin Mixture Following the general procedure of Example 1, a nitrogen-saturated solution of silver nitrate (0.25 M) in methanol, diglyme (3:1 v/v), is contacted with an equivolume amount of dehydrogenated $C_{10}$–$C_{14}$ n-paraffinic mixture estimated to contain 10% (v/v) $C_{10}$–$C_{14}$ olefins, mainly $C_{11}$ and $C_{12}$ internal olefins. The two-phase system is agitated continuously at 20°–25° C. for up to one hour. After separation of the two phases, the enriched olefin fraction is recovered from the extract phase by fractional distillation as described in Example 1, and then contacted with a further sample of silver salt solution. Again the olefin-enriched fraction is recovered from the extract phase by fractional distillation. The extraction procedure is repeated then for a third cycle. Final concentration of $C_{10}$–$C_{14}$ olefin in the extract phase after three cycles is 32%; data are summarized in Table I.

The paraffinic raffinate phase from the first extraction with silver nitrate solution is also contacted with a second equivolume mixture of $AgNO_3$ in methanol, diglyme and the two-phase mix separated after vigorous agitation for one hour. Once again the procedure is repeated, the final $C_{10}$–$C_{14}$ olefin concentration in the residual paraffinic phase being 4.3%. Extraction data for this second series of extractions are summarized in the second half of Table I.

Over a 3-cycle extraction of typical dehydrogenated $C_{10}$–$C_{14}$ n-paraffin mixture it may be noted that:

(a) The $C_{10}$–$C_{14}$ olefin content of the extract phase is steadily raised from about 10% up to 34%.

(b) The $C_{10}$–$C_{14}$ olefin content of the paraffinic, raffinate phase is steadily depleted from 10% down to 4.3%.

(c) β-Factor* values remain well above unity for both series of extractions, indicating that under the selected conditions, this extraction technique is an efficient means of enrichment.

*For definition of terms see: Diamond et al., "Progress in Inorganic Chemistry," Vol. 2, p. 112 (1960), and Davis, et al., "Separation and Purification Methods," Vol. I, p. 199 (1973).

EXAMPLES 4 TO 14

The Extraction of $C_{10}$–$C_{14}$ Olefins from $C_{10}$–$C_{14}$ n-Paraffin Mixtures with Various Group IB Metal Salts Under a Range of Experimental Conditions Following the general procedures of Example 1, nitrogen-saturated solutions of silver nitrate (0.125 M to 0.25 M) in methanol, 1,2-dimethoxyethane (3:1, v/v) are contacted with dehydrogenated $C_{10}$–$C_{14}$ n-paraffinic mixture containing 10% (v/v) $C_{10}$–$C_{14}$ olefins under the conditions specified in Table II. After separation of the two phases, the enriched olefin fraction is recovered from the extract phase by fractional distillation. Data are summarized in Table II, examples 4–8.

Similar data were obtained by substituting silver nitrate by the equivalent amount of silver acetate, silver fluoroborate, copper fluoride, copper 2-ethylhexanoate, copper acetylacetonate and silver propionate. Extraction data are also summarized in Table II, examples 9–14.

Extraction is carried out in accordance with the procedures outlined in Example 1, and the enriched 1-decene fraction is recovered from the extract phase by fractional distillation. Results are summarized below in Table III; selective removal of the 1-decene fraction is observed in all four experiments.

EXAMPLE 19

THE SELECTIVE EXTRACTION OF A 2-OCTENE, n-DODECANE MIXTURE

In this example, a mixture of 2-octene and n-dodecane containing 14.8% 2-octene is contacted with a solution of silver nitrate (0.25 M) in methanol, diglyme (3:1, v/v mixture). The two-phase liquid is agitated vigorously at ambient temperature (22° C.) for one hour, the extract phase removed and fractionally distilled to recover the 2-octene rich phase. Titre and glc analyses of the isolated 2-octene rich phase show an $C_8H_{16}$ content of 20 to 22%. The residual paraffinic (n-dodecane) phase shows a 2-octene content of 9.1 to 9.5%.

What is claimed is:

1. A liquid-liquid extraction process for the separation of aliphatic olefins from mixtures of olefinic and paraffinic hydrocarbons, said olefins and paraffins containing from 6 to 20 carbon atoms per molecule, and said process being carried out by:

a. Contacting said mixtures of olefins and paraffinic hydrocarbons from which the olefins are to be separated, with an extractant, non-aqueous solution of Group IB metal salts, said metal salts being selected from the group consisting of silver and copper salts, and said non-aqueous solvent systems being selected from alkanols containing from 1 to 4 carbon atoms, to form a two-phase mixture.

Table I

| | Multiple Extraction of $C_{10}$–$C_{14}$ Olefins from a $C_{10}$–$C_{14}$ n-Paraffin Mixture | | | |
|---|---|---|---|---|
| | $C_{10}$–$C_{14}$ Olefin conc. in paraffin phase (%) | | $C_{10}$–$C_{14}$ Olefin conc. in extract (%) | β-Factor |
| $C_{10}$–$C_{14}$ Olefin/paraffin charge mixture | Initial | After extraction | | |
| Dehydrogenated $C_{10}$–$C_{14}$ n-paraffin | 9.6 | 7.2 | 14.8 | 2.23 |
| Extract after 1 cycle | 14.8 | 12.6 | 24.8 | 2.29 |
| Extract after 2 cycles | 24.8 | 21.6 | 32.0 | 1.71 |
| Paraffinic raffinate after 1 cycle | 7.2 | 5.8 | 13.1 | 2.45 |
| Paraffinic raffinate after 2 cycles | 5.8 | 4.3 | 8.5 | 2.07 |

Table II

| | | | | | | $C_{10}$–$C_{14}$ olefin conc. in paraffinic phase (%) | | $C_{10}$–$C_{14}$ |
|---|---|---|---|---|---|---|---|---|
| | | | | Mole ratio of | | | | olefin conc. |
| Example | Complexing agent | Solvent | [M$^c$] (M) | [AgNO$_3$]/ [$C_{10}$–$C_{14}$ olefin] | Temp (° C) | Before extract | After extract | in extract (%) |
| 4 | AgNO$_3$ | MeOH/DME$^a$ | 0.25 | 1:1 | 22 | 9.6 | 6.7 | 13.9 |
| 5 | " | " | " | 1:2 | " | 9.6 | 8.0 | 18.6 |
| 6 | " | " | 0.125 | 1:2 | " | 9.6 | 7.4 | 15.2 |
| 7 | " | " | 0.25 | 1:1 | 40 | 8.6 | 6.4 | 11.2 |
| 8 | " | " | " | 1:1 | 60 | 8.6 | 6.8 | 10.0 |
| 9 | AgOAc | MeOH/diglyme | " | 1:1 | 22 | 9.6 | 7.6 | |
| 10 | AgBF$_4$ | MeOH/DME | " | 1:1 | " | 9.6 | 7.9 | |
| 11 | CuF$_2$ | " | " | 1:1 | " | 9.6 | 8.7 | |
| 12 | Cu(2-EH)$_2$$^b$ | " | " | 1:1 | " | 9.6 | 8.6 | |
| 13 | Cu(acac)$_2$ | " | " | 1:1 | " | 9.6 | 8.3 | |
| 14 | AgOPr | " | " | 1:1 | " | 9.6 | 6.7 | |

$^a$DME, 1,2-Dimethoxyethane.
$^b$2-EH, 2-Ethylhexanoate.
$^c$M = Ag or Cu.

EXAMPLES 15 to 18

THE SELECTIVE EXTRACTION OF 1-DECENE, n-DODECANE MIXTURES

In these four examples, mixtures of 1-decene and n-dodecane containing from 7.6 to 55% 1-decene are contacted with solutions of silver nitrate (0.25 M) in methanol or methanol, 1,2-dimethoxyethane mixture.

b. Agitating the two-phase mixture to form an extractant phase which is olefin rich and paraffin poor, and a paraffinic phase which is olefin poor, c. Separating the extractant, olefin-rich, phase from the paraffinic-rich phase and isolating the olefin concentrate contained within the extractant phase.

2. The process of claim 1 wherein the non-aqueous solvent system is composed of said alkanols containing 1 to 4 carbon atoms, in combination with a polyether solvent.

3. The process of claim 2 wherein the polyether solvent is selected from the group consisting of 1,2-dimethoxyethane, diethyleneglycol dimethyl ether, triethyleneglycol dimethyl ether and 1,2-diethoxyethane.

4. The process of claim 2 wherein the alkanol solvent is selected from the group consisting of methanol, ethanol and n-propanol.

5. The process of claim 1 wherein the silver salts employed in the extracting phase are selected from the group consisting of silver nitrate, silver acetate, silver fluoroborate and silver propionate.

6. The process of claim 1 wherein the copper salts employed in the extracting phase are selected from the group consisting of copper fluoride, copper 2-ethylhexanoate and copper acetylacetonate.

7. The process of claim 1 wherein the mixture of olefins and paraffins to be separated is composed of a mixture of 2-octene and n-dodecene.

8. The process of claim 1 wherein the mixture of olefins and paraffins to be separated is composed of 1-dodecene and n-dodecane.

9. The process of claim 1 wherein the mixtures of olefins and paraffin to be separated are derived from the dehydrogenation of n-paraffins.

10. The process of claim 9 wherein the mixtures of olefins and paraffins to be separated are obtained from the dehydrogenation of $C_{10}$–$C_{14}$ n-paraffins.

* * * * *